(12) United States Patent  
Kobayashi

(10) Patent No.: US 7,429,277 B2  
(45) Date of Patent: Sep. 30, 2008

(54) HAIR-DYEING AGENT

(75) Inventor: Katsumi Kobayashi, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 227 days.

(21) Appl. No.: 11/385,790

(22) Filed: Mar. 22, 2006

(65) Prior Publication Data

US 2006/0230547 A1 Oct. 19, 2006

(30) Foreign Application Priority Data

Mar. 23, 2005 (JP) ............................... 2005-084961

(51) Int. Cl.
*A61Q 5/10* (2006.01)
(52) U.S. Cl. ................... 8/405; 8/406; 8/463; 8/565; 8/568; 8/576; 8/607; 8/648
(58) Field of Classification Search ................ 8/405, 8/406, 463, 565, 568, 576, 607, 648
See application file for complete search history.

(56) References Cited

U.S. PATENT DOCUMENTS 6,329,165 B1 * 12/2001 Chattoraj et al. .............. 435/29

FOREIGN PATENT DOCUMENTS

| JP | 10-502946 A | 3/1998 |
|----|-------------|--------|
| WO | WO-97/20545 A1 | 6/1997 |

OTHER PUBLICATIONS

STIC Search Report dated Oct. 29, 2007.*

* cited by examiner

*Primary Examiner*—Eisa B Elhilo
(74) *Attorney, Agent, or Firm*—Birch, Stewart, Kolasch & Birch, LLP

(57) ABSTRACT

A hair-dyeing agent, which contains at least one compound represented by formula (1) or (2) as a dye:

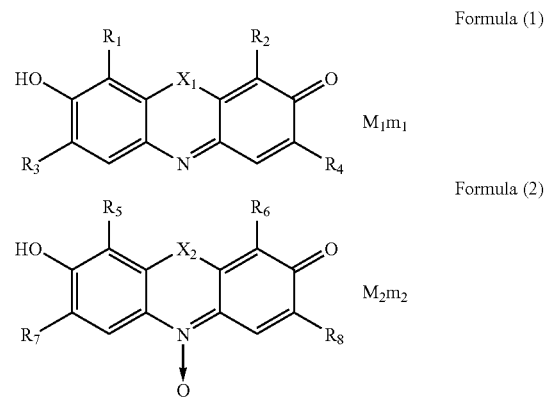

wherein $X_1$ and $X_2$ each are an oxygen atom, nitrogen atom, sulfur atom, or dialkylmethylene group; $R_1$, $R_2$, $R_3$, $R_4$, $R_5$, $R_6$, $R_7$, and $R_8$ each independently are a hydrogen atom or substituent; $M_1$ and $M_2$ each are a counter ion to balance the charge of the molecule; and $m_1$ and $m_2$ each are a number of 0 or more necessary to neutralize the charge of the molecule.

24 Claims, No Drawings

HAIR-DYEING AGENT

FIELD OF THE INVENTION

The present invention relates to a hair-dyeing or -coloring agent having excellent dyeing power, being capable of imparting vivid color in a wide range to the hair, and showing less color fade with the lapse of time.

BACKGROUND OF THE INVENTION

Hitherto, oxidative dyes have been used in permanent hair-dyeing or -coloring agents. The oxidative dye is allowed to penetrate into hairs in the state of a dye precursor, having a small size, which becomes oxidized in the hair, forming a dye molecule having a relatively large molecular size, thereby keeping the hair colored for a long period of time. However, this method has the problem that it is impossible to obtain the effect of dyeing hair in a fresh tone. Further, the safeties of a dye precursor itself, uncontrollable intermediates, and final products are currently regarded as problematic.

In the meanwhile, semi-permanent hair-dyeing or -coloring agents and temporary hair-dyeing or -coloring agents, that dye hair by applying a direct dye to hair, are used. However, these hair-dyeing agents have the drawbacks, e.g. that they have a shorter hair-color retention term, as their names imply, and that only insufficient hair-dyeing density. An attempt is made to use a nitro dye or a cationic dye as a direct dye to improve the hair-dyeing density in this method (see, for example, JP-A-6-271435 ("JP-A" means unexamined published Japanese patent application), JP-A-2001-261535, JP-T-8-501322 ("JP-T" means published searched patent publication), JP-T-8-507545, and JP-T-10-502946). However, when a nitro dye is used, it poses the problem that hair significantly fades with the lapse of time, and easily becomes darkish. On the other hand, when a cationic dye is used, it poses the problem that significant color fading is caused by shampooing hair, depending on the type of dye.

SUMMARY OF THE INVENTION

The present invention resides in a hair-dyeing agent, which comprises at least one compound represented by the following formula (1) as a dye:

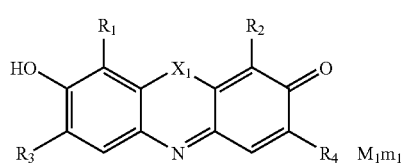

Formula (1)

wherein $X_1$ represents an oxygen atom, a nitrogen atom, a sulfur atom, or a dialkylmethylene group; $R_1$, $R_2$, $R_3$, and $R_4$ each independently represent a hydrogen atom or a substituent; $M_1$ represents a counter ion to balance the charge of the molecule; and $m_1$ denotes a number of 0 or more necessary to neutralize said charge of the molecule.

The present invention also resides in a hair-dyeing agent, which comprises at least one compound represented by the following formula (2) as a dye:

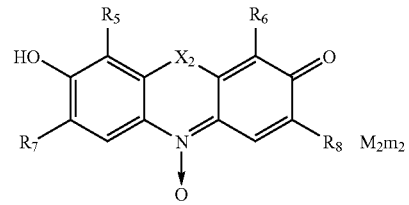

Formula (2)

wherein $X_2$ represents an oxygen atom, a nitrogen atom, a sulfur atom, or a dialkylmethylene group; $R_5$, $R_6$, $R_7$, and $R_8$ each independently represent a hydrogen atom or a substituent; $M_2$ represents a counter ion to balance the charge of the molecule; and $m_2$ denotes a number of 0 or more necessary to neutralize said charge of the molecule.

Other and further features and advantages of the invention will appear more fully from the following description.

DETAILED DESCRIPTION OF THE INVENTION

According to the present invention, there is provided the following means:
(1) A hair-dyeing agent, comprising at least one compound represented by formula (1) as a dye, preferably as a direct dye:

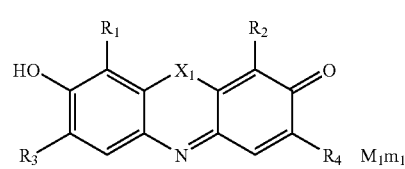

Formula (1)

wherein $X_1$ represents an oxygen atom, a nitrogen atom, a sulfur atom, or a dialkylmethylene group; $R_1$, $R_2$, $R_3$, and $R_4$ each independently represent a hydrogen atom or a substituent; $M_1$ represents a counter ion to balance the charge of the molecule; and $m_1$ denotes a number of 0 or more necessary to neutralize said charge of the molecule; and
(2) A hair-dyeing agent, comprising at least one compound represented by formula (2) as a dye, preferably as a direct dye:

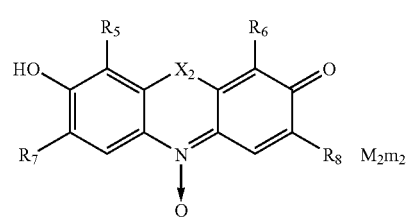

Formula (2)

wherein $X_2$ represents an oxygen atom, a nitrogen atom, a sulfur atom, or a dialkylmethylene group; $R_5$, $R_6$, $R_7$, and $R_8$ each independently represent a hydrogen atom or a substituent; $M_2$ represents a counter ion to balance the charge of the molecule; and $m_2$ denotes a number of 0 or more necessary to neutralize said charge of the molecule.

The best mode for carrying out the present invention is described in detail below.

In the compound that can be used in the present invention, when a specific moiety is referred to as "group (or substituent)", said moiety means that it per se may be unsubstituted or substituted by one or more (to the greatest possible number of) kinds of substituents. For example, "an alkyl group" as a substituent means a substituted or unsubstituted alkyl group. Accordingly, the substituent that can substitute on the compound for use in the present invention may be any substituent, regardless of any other further substituent thereon, unless otherwise specified.

When the substituent is represented by "W", there is no particular limitation on the substituent represented by W. Examples of the substituent represented by W include: a halogen atom; an alkyl group [(including a cycloalkyl group, a bicycloalkyl group, and a tricycloalkyl group); and also including: an alkenyl group (including a cycloalkenyl group and a bicycloalkenyl group), and an alkynyl group]; an aryl group; a heterocyclic group (also referred to as a heterocycle); a cyano group; a hydroxyl group; a nitro group; a carboxyl group; an alkoxy group; an aryloxy group; a silyloxy group; a heterocyclic oxy group; an acyloxy group; a carbamoyloxy group; an alkoxycarbonyloxy group; an aryloxycarbonyloxy group; an amino group (including an anilino group); an ammonio group; an acylamino group; an aminocarbonylamino group; an alkoxycarbonylamino group; an aryloxycarbonylamino group; a sulfamoylamino group; an alkyl- or aryl-sulfonylamino group; a mercapto group; an alkylthio group; an arylthio group; a heterocyclic thio group; a sulfamoyl group; a sulfo group; an alkyl- or aryl-sulfinyl group; an alkyl- or aryl-sulfonyl group; an acyl group; an alkoxycarbonyl group; an aryloxycarbonyl group; a carbamoyl group; an aryl- or heterocyclic-azo group; an imido group; a phosphino group; a phosphinyl group; a phosphinyloxy group; a phosphinylamino group; a phosphono group; a silyl group; a hydrazino group; a ureido group; and other known substituents.

Specific examples of W include: a halogen atom (e.g. a fluorine atom, a chlorine atom, a bromine atom, or an iodine atom); an alkyl group [which represents a substituted or unsubstituted linear, branched, or cyclic alkyl group, and which includes an alkyl group (preferably an alkyl group having 1 to 30 carbon atoms, e.g. a methyl group, an ethyl group, an n-propyl group, an isopropyl group, a t-butyl group, an n-octyl group, an eicosyl group, a 2-chloroethyl group, a 2-cyanoethyl group, or a 2-ethylhexyl group), a cycloalkyl group (preferably a substituted or unsubstituted cycloalkyl group having 3 to 30 carbon atoms, e.g. a cyclohexyl group, a cyclopentyl group, or a 4-n-dodecylcyclohexyl group), a bicycloalkyl group (preferably a substituted or unsubstituted bicycloalkyl group having 5 to 30 carbon atoms, e.g. a bicyclo[1.2.2]heptan-2-yl group or a bicyclo[2.2.2]octan-3-yl group), and a tricyclo or higher structure having three or more ring structures; and an alkyl group in a substituent described below (e.g. an alkyl group in an alkylthio group) represents such an alkyl group of the above concept, but it may also include an alkenyl group, a cycloalkenyl group, a bicycloalkenyl group, or an alkynyl group]; an alkenyl group [which represents a substituted or unsubstituted linear, branched, or cyclic alkenyl group, and which includes an alkenyl group (preferably a substituted or unsubstituted alkenyl group having 2 to 30 carbon atoms, e.g. a vinyl group, an allyl group, a prenyl group, a geranyl group, or an oleyl group), a cycloalkenyl group (preferably a substituted or unsubstituted cycloalkenyl group having 3 to 30 carbon atoms, e.g. a 2-cyclopenten-1-yl group or a 2-cyclohexen-1-yl group), and a bicycloalkenyl group (which represents a substituted or unsubstituted bicycloalkenyl group, preferably a substituted or unsubstituted bicycloalkenyl group having 5 to 30 carbon atoms, e.g. a bicyclo[2.2.1]hept-2-en-1-yl group or a bicyclo[2.2.2]oct-2-en-4-yl group)]; an alkynyl group (preferably a substituted or unsubstituted alkynyl group having 2 to 30 carbon atoms, e.g. an ethynyl group, a propargyl group, or a trimethylsilylethynyl group); an aryl group (preferably a substituted or unsubstituted aryl group having 6 to 30 carbon atoms, e.g. a phenyl group, a p-tolyl group, a naphthyl group, an m-chlorophenyl group, or an o-hexadecanoylaminophenyl group); a heterocyclic group (preferably a monovalent group obtained by removing one hydrogen atom from a substituted or unsubstituted 5- or 6-membered aromatic or nonaromatic heterocyclic compound; more preferably a 5- or 6-membered aromatic heterocyclic group having 3 to 30 carbon atoms, e.g. a 2-furyl group, a 2-thienyl group, a 2-pyrimidinyl group, a 2-benzothiazolyl group, or a cationic heterocyclic group, e.g. a 1-methyl-2-pyridinio group or a 1-methyl-2-quinolinio group); a cyano group; a hydroxyl group; a nitro group; a carboxyl group; an alkoxy group (preferably a substituted or unsubstituted alkoxy group having 1 to 30 carbon atoms, e.g. a methoxy group, an ethoxy group, an isopropoxy group, a t-butoxy group, an n-octyloxy group, or a 2-methoxyethoxy group); an aryloxy group (preferably a substituted or unsubstituted aryloxy group having 6 to 30 carbon atoms, e.g. a phenoxy group, a 2-methylphenoxy group, a 4-t-butylphenoxy group, a 3-nitrophenoxy group, or a 2-tetradecanoylaminophenoxy group); a silyloxy group (preferably a silyloxy group having 3 to 20 carbon atoms, e.g. a trimethylsilyloxy group or a t-butyldimethylsilyloxy group); a heterocyclic oxy group (preferably a substituted or unsubstituted heterocyclic oxy group having 2 to 30 carbon atoms, e.g. a 1-phenyltetrazol-5-oxy group or a 2-tetrahydropyranyloxy group); an acyloxy group (preferably a formyloxy group, a substituted or unsubstituted alkylcarbonyloxy group having 2 to 30 carbon atoms, or a substituted or unsubstituted arylcarbonyloxy group having 7 to 30 carbon atoms, e.g. a formyloxy group, an acetyloxy group, a pivaloyloxy group, a stearoyloxy group, a benzoyloxy group, or a p-methoxyphenylcarbonyloxy group); a carbamoyloxy group (preferably a substituted or unsubstituted carbamoyloxy group having 1 to 30 carbon atoms, e.g. an N,N-dimethylcarbamoyloxy group, an N,N-diethylcarbamoyloxy group, a morpholinocarbonyloxy group, an N,N-di-n-octylaminocarbonyloxy group, or an N-n-octylcarbamoyloxy group); an alkoxycarbonyloxy group (preferably a substituted or unsubstituted alkoxycarbonyloxy group having 2 to 30 carbon atoms, e.g. a methoxycarbonyloxy group, an ethoxycarbonyloxy group, a t-butoxycarbonyloxy group, or an n-octylcarbonyloxy group); an aryloxycarbonyloxy group (preferably a substituted or unsubstituted aryloxycarbonyloxy group having 7 to 30 carbon atoms, e.g. a phenoxycarbonyloxy group, a p-methoxyphenoxycarbonyloxy group, or a p-n-hexadecyloxyphenoxycarbonyloxy group); an amino group (preferably an amino group, a substituted or unsubstituted alkylamino group having 1 to 30 carbon atoms, or a substituted or unsubstituted anilino group having 6 to 30 carbon atoms, e.g. an amino group, a methylamino group, a dimethylamino group, an anilino group, an N-methyl-anilino group, or a diphenylamino group); an ammonio group (preferably an ammonio group, or an ammonio group substituted by a substituted or unsubstituted alkyl group, aryl group, or hetero ring having 1 to 30 carbon atoms, e.g. a trimethylammonio group, a triethylammonio group, or a diphenylmethylammonio group); an acylamino group (preferably a formylamino group, a substituted or unsubstituted alkylcarbonylamino group having 1 to 30 carbon atoms, or a substituted or unsubstituted arylcarbonylamino group having 6 to 30 carbon atoms, e.g. a formylamino group, an acetylamino group, a pivaloylamino group, a lauroylamino group, a benzoylamino group, or a 3,4,5-tri-n-octyloxyphenylcarbonylamino group); an aminocarbonylamino group (preferably a substituted or unsubstituted aminocarbonylamino group having 1 to 30 carbon atoms, e.g. a carbamoylamino group, an N,N-dimethylaminocarbonylamino group, an N,N-diethylaminocarbonylamino group, or a morpholinocarbonylamino group); an alkoxycarbonylamino group (preferably a substituted or unsubstituted alkoxycarbonylamino group having 2 to 30 carbon atoms, e.g. a methoxycarbonylamino group, an ethoxycarbonylamino group, a t-butoxycarbonylamino group, an n-octadecyloxycarbonylamino group, or an N-methyl-methoxycarbonylamino group); an aryloxycarbonylamino group (preferably a substituted or unsubstituted aryloxycarbonylamino group having 7 to 30 carbon atoms, e.g. a phenoxycarbonylamino group, a p-chlorophenoxycarbonylamino group, or an m-n-octyloxyphenoxycarbonylamino group); a sulfamoylamino group (preferably a substituted or unsubstituted sulfamoylamino group having 0 to 30 carbon atoms, e.g. a sulfamoylamino group, an N,N-dimethylaminosulfonylamino group, or an N-n-octylaminosulfonylamino group); an alkyl- or aryl-sulfonylamino group (preferably a substituted or unsubstituted alkylsulfonylamino group having 1 to 30 carbon atoms, or a substituted or unsubstituted arylsulfonylamino group having 6 to 30 carbon atoms, e.g. a methylsulfonylamino group, a butylsulfonylamino group, a phenylsulfonylamino group, a 2,3,5-trichlorophenylsulfonylamino group, or a p-methylphenylsulfonylamino group); a mercapto group; an alkylthio group (preferably a substituted or unsubstituted alkylthio group having 1 to 30 carbon atoms, e.g. a methylthio group, an ethylthio group, or an n-hexadecylthio group); an arylthio group (preferably a substituted or unsubstituted arylthio group having 6 to 30 carbon atoms, e.g. a phenylthio group, a p-chlorophenylthio group, or an m-methoxyphenylthio group); a heterocyclic thio group (preferably a substituted or unsubstituted heterocyclic thio group having 2 to 30 carbon atoms, e.g. a 2-benzothiazolyl thio group or a 1-phenyltetrazol-5-yl thio group); a sulfamoyl group (preferably a substituted or unsubstituted sulfamoyl group having 0 to 30 carbon atoms, e.g. an N-ethylsulfamoyl group, an N-(3-dodecyloxypropyl)sulfamoyl group, an N,N-dimethylsulfamoyl group, an N-acetylsulfamoyl group, an N-benzoylsulfamoly group, or an N-(N'-phenylcarbamoyl)sulfamoyl group); a sulfo group; an alkyl- or aryl-sulfinyl group (preferably a substituted or unsubstituted alkylsulfinyl group having 1 to 30 carbon atoms, or a substituted or unsubstituted arylsulfinyl group having 6 to 30 carbon atoms, e.g. a methylsulfinyl group, an ethylsulfinyl group, a phenylsulfinyl group, or a p-methylphenylsulfinyl group); an alkyl- or aryl-sulfonyl group (preferably a substituted or unsubstituted alkylsulfonyl group having 1 to 30 carbon atoms, or a substituted or unsubstituted arylsulfonyl group having 6 to 30 carbon atoms, e.g. a methylsulfonyl group, an ethylsulfonyl group, a phenylsulfonyl group, or a p-methylphenylsulfonyl group); an acyl group (preferably a formyl group, a substituted or unsubstituted alkylcarbonyl group having 2 to 30 carbon atoms, a substituted or unsubstituted arylcarbonyl group having 7 to 30 carbon atoms, or a substituted or unsubstituted heterocyclic carbonyl group having 4 to 30 carbon atoms and being bonded to said carbonyl group through a carbon atom, e.g. an acetyl group, a pivaloyl group, a 2-chloroacetyl group, a stearoyl group, a benzoyl group, a p-n-octyloxyphenylcarbonyl group, a 2-pyridylcarbonyl group, or a 2-furylcarbonyl group); an aryloxycarbonyl group (preferably a substituted or unsubstituted aryloxycarbonyl group having 7 to 30 carbon atoms, e.g. a phenoxycarbonyl group, an o-chlorophenoxycarbonyl group, an m-nitrophenoxycarbonyl group, or a p-t-butylphenoxycarbonyl group); an alkoxycarbonyl group (preferably a substituted or unsubstituted alkoxycarbonyl group having 2 to 30 carbon atoms, e.g. a methoxycarbonyl group, an ethoxycarbonyl group, a t-butoxycarbonyl group, or an n-octadecyloxycarbonyl group); a carbamoyl group (preferably a substituted or unsubstituted carbamoyl group having 1 to 30 carbon atoms, e.g. a carbamoyl group, an N-methylcarbamoyl group, an N,N-dimethylcarbamoyl group, an N,N-di-n-octylcarbamoyl group, or an N-(methylsulfonyl)carbamoyl group); an aryl- or heterocyclic-azo group (preferably a substituted or unsubstituted aryl azo group having 6 to 30 carbon atoms, or a substituted or unsubstituted heterocyclic azo group having 3 to 30 carbon atoms, e.g. a phenylazo group, a p-chlorophenylazo group, or a 5-ethylthio-1,3,4-thiadiazol-2-ylazo group); an imido group (preferably an N-succinimido group, or an N-phthalimido group); a phosphino group (preferably a substituted or unsubstituted phosphino group having 2 to 30 carbon atoms, e.g. a dimethylphosphino group, a diphenylphosphino group, or a methylphenoxyphosphino group); a phosphinyl group (preferably a substituted or unsubstituted phosphinyl group having 2 to 30 carbon atoms, e.g. a phosphinyl group, a dioctyloxyphosphinyl group, or a diethoxyphosphinyl group); a phosphinyloxy group (preferably a substituted or unsubstituted phosphinyloxy group having 2 to 30 carbon atoms, e.g. a diphenoxyphosphinyloxy group or a dioctyloxyphosphinyloxy group); a phosphinylamino group (preferably a substituted or unsubstituted phosphinylamino group having 2 to 30 carbon atoms, e.g. a dimethoxyphosphinylamino group or a dimethylaminophosphinylamino group); a phospho group; a silyl group (preferably a substituted or unsubstituted silyl group having 3 to 30 carbon atoms, e.g. a trimethylsilyl group, a t-butyldimethylsilyl group, or a phenyldimethylsilyl group); a hydrazino group (preferably a substituted or unsubstituted hydrazino group having 0 to 30 carbon atoms, e.g. a trimethylhydrazino group); and a ureido group (preferably a substituted or unsubstituted ureido group having 0 to 30 carbon atoms, e.g. an N,N-dimethylureido group).

Two substituents W in combination may bond together to form a ring (an aromatic or nonaromatic, hydrocarbon ring or hetero ring, or a combination thereof forming a polycyclic condensed ring, examples of which include a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiine ring, a phenothiazine ring, or a phenazine ring).

Among the substituents W, with respect to one having a hydrogen atom, the hydrogen atom may be removed and be substituted by any of the above-mentioned substituents. Examples of such a composite substituent include an acylsulfamoyl group, and an alkyl- or aryl-sulfonylcarbamoyl group. Examples thereof include a methylsulfonylcarbamoyl group, a p-methylphenylsulfonylcarbamoyl group, an acetylsulfamoyl group, and a benzoylsulfamoyl group.

The compound represented by formula (1) or (2) that can be used in the present invention will be explained in detail below.

In the hair-dyeing agent of the present invention, the compound represented by formula (1) or (2) is used as a dye, preferably as a direct dye.

$X_1$ and $X_2$ each independently represent an oxygen atom, a nitrogen atom, a sulfur atom, or a dialkylmethylene group. $X_1$ and $X_2$ each preferably represent an oxygen atom or a nitrogen atom, and particularly preferably represent an oxygen atom. When $X_1$ and $X_2$ each independently represent a dialkylmethylene group, $X_1$ and $X_2$ are preferably a dimethylmethylene group.

$R_1$, $R_2$, $R_3$, $R_4$, $R_5$, $R_6$, $R_7$, and $R_8$ each independently represent a hydrogen atom or a substituent, and preferably a hydrogen atom. When $R_1$, $R_2$, $R_3$, $R_4$, $R_5$, $R_6$, $R_7$, and $R_8$ each independently represent a substituent, examples of the substituent include the examples of the above substituent W, and preferable examples thereof include a halogen atom, alkyl group, hydroxyl group, amino group, alkoxy group, alkylthio group, aryloxy group, arylthio group, acyl group, cyano group, or nitro group. More preferable examples of the substituent include a halogen atom, hydroxyl group, amino group, alkoxy group, alkylthio group, aryloxy group, acyl group, cyano group, or nitro group.

$M_1$ or $M_2$ is included in the formula to show the presence of a cation or anion, when it is necessary to neutralize the ionic charge of the dye. Whether a dye is a cation or an anion or has a net ionic charge, is dependent on the type of substituent and on the conditions (pH) of the solution. Typical examples of the cation include inorganic cation, e.g. hydrogen ion ($H^+$), alkali metal ion (e.g., sodium ion, potassium ion, lithium ion), and alkaline earth metal ion (e.g., calcium ion); and organic cation, e.g. ammonium ion (e.g., ammonium ion, tetraalkylammonium ion, triethylammonium ion, pyridinium ion, ethylpyridinium ion, 1,8-diazabicyclo[5.4.0]-7-undecenium ion). The anion may be either inorganic anion or organic anion, and examples thereof include halide anion (e.g., fluoride ion, chloride ion, bromide ion, iodide ion), substituted arylsulfonate ion (e.g., p-toluenesulfonate ion, p-chlorobenzenesulfonate ion), aryldisulfonate ion (e.g., 1,3-benzenesulfonate ion, 1,5-naphthalenedisulfonate ion, 2,6-naphthalenedisulfonate ion), alkylsulfate ion (e.g., methylsulfate ion), sulfate ion, thiocyanate ion, perchlorate ion, tetrafluoroborate ion, picrate ion, acetate ion, and trifluoromethanesulfonate ion. Also, an ionic polymer or another dye having a charge opposite to the dye may be used. Preferable examples of the cation include sodium ion, potassium ion, triethylammonium ion, tetraethylammonium ion, pyridinium ion, ethylpyridinium ion, and methylpyridinium ion. Preferable examples of the anion include perchloric acid ion, iodide ion, bromide ion, and substituted arylsulfonic acid ion (for example, a p-toluenesulfonic acid ion).

$m_1$ and $m_2$ each represent a number of 0 or more that is necessary for balancing the electric charge, preferably a number of 0 to 4, and when an inner salt is formed, $m_1$ and $m_2$ each are 0.

A preferable embodiment of the compound represented by formula (1) that can be used in the present invention will be explained.

The compound represented by formula (1) that can be used in the present invention is preferably those in which $R_1$, $R_2$, $R_3$ and $R_4$ each independently represent a hydrogen atom or a halogen atom.

The compound represented by formula (1) that can be used in the present invention is more preferably those in which $R_1$, $R_2$, $R_3$ and $R_4$ each independently represent a hydrogen atom or a halogen atom, and $X_1$ represents an oxygen atom or a dialkylmethylene group.

A preferable embodiment of the compound represented by formula (2) that can be used in the present invention will be explained.

The compound represented by formula (2) that can be used in the present invention is preferably those in which $R_5$, $R_6$, $R_7$ and $R_8$ each independently represent a hydrogen atom or a halogen atom.

The compound represented by formula (2) that can be used in the present invention is more preferably those in which $R_5$, $R_6$, $R_7$ and $R_8$ each independently represent a hydrogen atom or a halogen atom, and $X_2$ represents an oxygen atom or a dialkylmethylene group.

Next, specific examples of the compound represented by formula (1) that can be used in the present invention will be shown, but the present invention is not limited thereto.

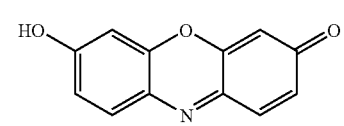

1-1

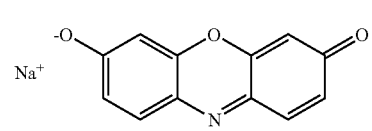

1-2

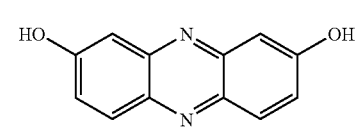

1-3

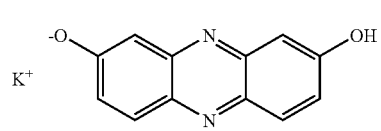

1-4

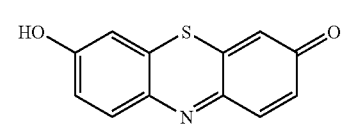

1-5

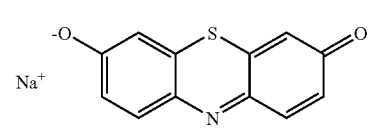

1-6

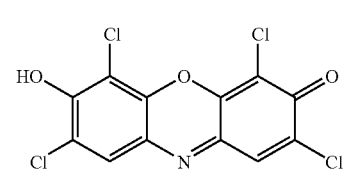

1-7

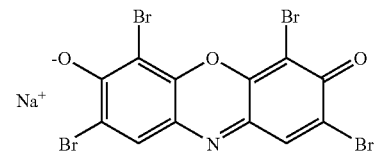

1-8

-continued

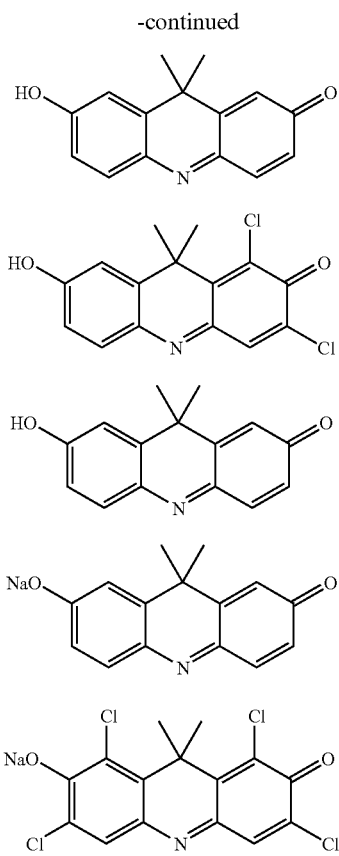

Next, specific examples of the compound represented by formula (2) that can be used in the present invention will be shown, but the present invention is not limited thereto.

-continued

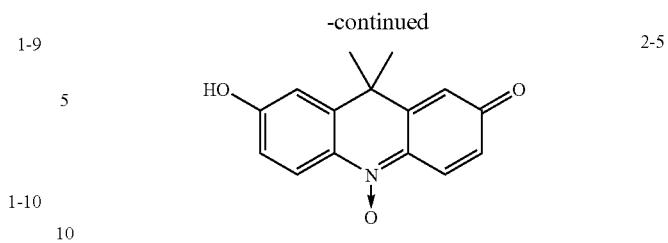

The compounds represented by formula (1) or (2) can be synthesized based on each method described, for example, in JP-A-62-36368, Science of Synthesis, vol. 17, pp. 117-221 (2004), Science of Synthesis, vol. 16, pp. 913-943 (2004), U.S. Pat. No. 3,740,403, and Agricultural and Biological Chemistry, vol. 36, p. 838 (1970).

In the present invention, "hair dyeing agent" means to include not only agents composed of a specific hair-dyeing or -coloring compound singly but also mixtures of the specific hair-dyeing compound and other hair-dyeing compound(s) or mixtures that are compositions of a hair-dyeing compound, an adjuvant, and a solvent; and further include not only hair-dying agents consisted of a single component part but also those composed of a set of two or more component parts provided in separate material forms, as will be explained later.

The hair-dyeing agent of the present invention may be used in combination with a direct dye(s) or oxidative dye(s) other than the compound represented by formula (1) or (2) according to the present invention.

Examples of such a direct dye include Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C.I. 11055), Basic Red 46 (C.I. 110825), Basic Red 76 (C.I. 12245), Basic Red 118 (C.I. 12251:1), Basic Yellow 28 (C.I. 48054), and Basic Yellow 57 (C.I. 12719); cationic dyes as described in JP-A-58-2204, JP-A-9-118832, JP-T-8-501322 and JP-T-8-507545.

The amount to be added of the compound represented by formula (1) or (2) in the hair-dyeing agent of the present invention, is preferably within the range of 0.0001 to 20 mass %, more preferably 0.001 to 20 mass %, further preferably from 0.05 to 10 mass %, especially preferably from 0.1 to 5 mass %, based on the whole composition (after mixing of all the component parts when the composition is a two part or three part composition; this will be applied similarly hereinafter). When another direct dye is used in combination, the total content of the dissociative direct dye (1) or (2) and the another direct dye preferably within the range from 0.001 to 20 mass %, more preferably from 0.01 to 20 mass %, still more preferably from 0.05 to 10 mass %, especially preferably from 0.1 to 5 mass %, based on the whole composition.

Since the compound represented by formula (1) or (2) according to the present invention exhibits a high storage stability within a wide pH range from 2 to 11, which is a pH range employed ordinarily for hair dyes, the hair-dyeing agent of the present invention can be used at any pH in the above-described pH range. In particular, use in a pH range of from 5 or greater is preferred, from the viewpoint of dyeing property.

The hair-dyeing agent of the present invention may contain various components other than the compound represented by formula (1) or (2).

Examples of the alkali agent that can be used in the hair-dyeing agent of the present invention include ammonia;

alkanolamines, e.g. monoethanolamine, isopropanolamine, or salts thereof; guanidium salts, e.g. guanidine carbonate; and hydroxides, e.g. sodium hydroxide. The alkali agent is added preferably in an amount of from 0.01 to 20 mass %, more preferably 0.1 to 10 mass %, especially preferably 0.5 to 5 mass %, based on the whole composition.

Since the compound represented by formula (1) or (2) for use in the hair-dyeing agent of the present invention has a high stability against an oxidizing agent, it can be applied to the hair after mixing with an oxidizing agent. In other words, in one embodiment, the hair-dyeing agent of the present invention can be provided as a two component parts composed of a first part containing the compound represented by formula (1) or (2) and a second part containing an oxidizing agent, each of which is provided separately. In that case, hair-dyeing and hair-bleaching or decolorizing can be carried out simultaneously, which facilitates more vivid color of the hair dyed.

Examples of the oxidizing agent include hydrogen peroxide; persulfates, e.g. ammonium persulfate, potassium persulfate, and sodium persulfate; perborates, e.g. sodium perborate; percarbonates, e.g. sodium percarbonate; and bromates, e.g. sodium bromate, and potassium bromate. Among those, hydrogen peroxide is especially preferred, from the viewpoints of hair bleaching property, and stability and effectiveness of the compound represented by formula (1) or (2) thereto. Further, hydrogen peroxide may be used in combination with another oxidizing agent(s). The oxidizing agent is added preferably in an amount of from 0.5 to 10 mass %, especially preferably from 1 to 8 mass %, based on the whole composition.

The first component part containing the compound represented by formula (1) or (2) and the second component part containing the oxidizing agent are mixed in a volume ratio preferably within the range from 2:1 to 1:3.

In the hair-dyeing agent of the present invention, an oxidative dye can be used in combination with the compound represented by formula (1) (or (2)). Such combined use enables considerably vivid and intense dyeing, which cannot be accomplished by the single use of the oxidative dye. For the oxidative dye, use can be made of any of known developers (color-developing substances) and couplers (coupling substances), each of which are ordinarily employed for an oxidation-type hair-dyeing agent.

Examples of the developer include para-phenylenediamine, toluene-2,5-diamine, 2-chloro-para-phenylenediamine, N-methoxyethyl-para-phenylenediamine, N,N-bis(2-hydroxyethyl)-para-phenylenediamine, 2-(2-hydroxyethyl)-para-phenylenediamine, 2,6-dimethyl-para-phenylenediamine, 4,4'-diaminodiphenylamine, 1,3-bis(N-(2-hydroxyethyl)-N-(4-aminophenyl)amino)-2-propanol, PEG-3,2,2'-para-phenylenediamine, para-aminophenol, para-methylaminophenol, 3-methyl-4-aminophenol, 2-aminomethyl-4-aminophenol, 2-(2-hydroxyethylaminomethyl)-4-aminophenol, orthoaminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraminopyrimidine, 2,5,6-triamino-4-hydroxypyrimidine, 4,5-diamino-1-(4'-chlorobenzyl)pyrazole, and salts thereof.

Examples of the coupler include meta-phenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, meta-aminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-meta-aminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, 2,6-diaminopyridine, and salts thereof.

As each of the developer and coupler, at least two of the above-described developers or couplers may be used in combination. The content of each of them is preferably from 0.01 to 20 mass %, especially preferably from 0.5 to 10 mass %, based on the whole composition.

To the hair-dyeing agent of the present invention, an autoxidative dye typified by indoles or indolines, or a known direct dye, e.g. a nitro dye or a disperse dye, can also be added.

Addition of a polyol, polyol alkyl ether, cationic or amphoteric polymer, or silicone to the hair-dyeing agent of the present invention is preferred, because the resulting composition can dye the hair uniformly and have improved cosmetic effects of the hair.

To the hair-dyeing agent of the present invention, in addition to the above-described components, those ordinarily employed as a raw material for cosmetics may be optionally added. Examples of such an optional component include hydrocarbons, animal or vegetable fats and oils, higher fatty acids, organic solvents, penetration accelerators, cationic surfactants, natural or synthetic polymers, higher alcohols, ethers, amphoteric surfactants, nonionic surfactants, anionic surfactants, protein derivatives, amino acids, antiseptics, chelating agents, stabilizers, antioxidants, plant extracts, crude drug extracts, vitamins; colorants, including dyes, pigments, and dye stuffs; perfumes, and ultraviolet absorbers.

The hair-dyeing agent of the present invention can be prepared according to a usual manner, which may have a form of a one-part agent, a two-part agent having a first agent component part containing an alkali agent and a second agent component part containing an oxidizing agent, or a three-part agent having, in addition to the aforementioned two parts, a powdery oxidizing agent, e.g. persulfate. The compound represented by formula (1) or (2) may be incorporated in at least one of the parts of the two-part or three-part agent. In the case of the two-part or three-part agent, the compound represented by formula (1) or (2) may be incorporated in at least one of the hair-dyeing agent component parts. The hair-dyeing agent of the present invention may be used in the following manner: When the hair-dyeing agent of the present invention is of a one-part type, the hair is coated with it directly, or alternatively when it is of a two- or three-part type, both or all the parts are mixed upon hair-dyeing and the hair is coated with the resultant mixture.

When preparing the hair-dyeing agent of the present invention as a two-part type, typically, the first part is prepared by blending the compound represented by formula (1) (or (2)) and optionally an oxidative dye and adjusting the pH thereof to 8 to 12 with an alkali agent, e.g. ammonia. The second part is prepared by incorporating about 2 to 6 mass % of hydrogen peroxide, adjusting the resultant to weakly acidic with phosphoric acid or the like. Alternatively, when preparing the hair-dyeing agent of the present invention as a three-part type, a persulfate is mixed with a binder or inert substance, e.g. talc or dextrin, to convert the mixture into a particulate form containing about 5 to 95 mass % of said persulfate. The resultant particulate third part is added to a mixture of the first part and the second part upon use.

The hair-dyeing agent of the present invention can be provided in the form of powder, transparent liquid, emulsion, cream, gel, paste, aerosol, aerosol foam, or the like. The hair-dyeing agent of the present invention preferably has a viscosity of 2,000 to 100,000 mPa·s upon its application to the hair (after mixing of all the parts when the agent is a two-part or three-part type). Herein, the viscosity is a value measured at 20° C. by using a Brookfield rotary viscometer (No. 5 spindle, 5 rpm).

According to the present invention, it is possible to provide a hair-dyeing agent that can dye hair intensely in a vivid tone, and that has high dyeing ability and is resistant to fading of the resultant color dyed with the lapse of time; and also a hair-dyeing method using this hair-dyeing agent.

Further, according to the present invention, it is possible to provide a hair-dyeing agent in which a dye is not decomposed in a hair-dyeing process, and that has high dyeing ability and is resistant to fading of the resultant color dyed with the lapse of time; and also a hair-dyeing method using this hair-dyeing agent.

Further, the hair-dyeing agent of the present invention has sufficient dyeing ability and high ability to retain the dyed color of hair against shampooing. Further, since the compound represented by formula (1) or (2) is sufficiently stable against an oxidizing agent, the hair-dyeing agent of the present invention can be used as a hair-dyeing agent to be used together with an oxidizing agent, to dye hair in a vivid color, while bleaching or decolorizing the hair.

The present invention will be described in more detail based on the following examples, but the invention is not intended to be limited thereto.

EXAMPLES

Example 1

Example Concerning the Dyeing Characteristics of a Dyeing Component

Each dye described in Table 1 was dissolved in a water-base composition containing an alkaline peroxide, to prepare a hair-dyeing agent having the following formulation, and the resultant hair-dyeing agent was applied to goat hair.

| [Formulation] | |
|---|---|
| Dye (one described in Table 1) | 0.2 g |
| Benzyl alcohol | 5.0 g |
| Sodium lauryl sulfate | 0.01 g |
| Ammonium hydroxide (25 mass %) | 5.0 g |
| Hydrogen peroxide (50 mass %) | 6.0 g |
| Water | Amount required for the total amount to be 100 g |
| pH | 10.0 |

The dye mixture was applied to white goat hair, having no damage, at 27° C. for 18 minutes. The composition having the formulation was applied in an amount of 1.5 to 2.0 g per 1 g of goat hair. After the dyeing time was ended, each bundle of the resultant hairs was washed with water, shampooed, and dried. After that, the color of the bundle of hairs was measured. With respect to each of the examples and comparative examples, the values L*, a*, and b* of the bundle of hairs, both before and after the coloring treatment, were measured by a color measuring meter (manufactured by Minolta), to calculate the values of ΔL* and ΔE* according to the following well-known equation (hereinafter, the same procedures are applied to all of the following examples and comparative examples).

$$\Delta E^*_{ab} = \{(\Delta L^*)^2 + (\Delta a^*)^2 + (\Delta b^*)^2\}^{1/2}$$

The results are shown in Table 1.

From the results in Table 1, the following can be understood: The hair-dyeing agents for comparison 1 and 2 each showed almost no difference in luminosity ΔL* and showed color differences ΔE as relatively small as 3 and 2, respectively, before and after the coloring treatment.

Contrary to the above, the hair-dyeing agents 3 to 6, of the present invention, each showed relatively large negative values as the differences in luminosity ΔL*, showing that the hair were darkened by the coloring treatment using, and also they each showed remarkably large ΔE*$_{ab}$ within the range from 13 to 31. Namely, the results according to the present invention showed thickly dyed hair.

TABLE 1

| Hair-dyeing agent | Dye | Color of goat hair after being dyed | ΔL* | ΔE*$_{ab}$ | Remarks |
|---|---|---|---|---|---|
| 1 | Dye for comparison 1 | Yellow | −1 | 3 | Comparative example |
| 2 | Dye for comparison 2 | Bluish purple | 0 | 2 | Comparative example |
| 3 | 1-1 | Pink | −3 | 20 | This invention |
| 4 | 1-8 | Blue | −5 | 13 | This invention |
| 5 | 1-10 | Blue | −12 | 31 | This invention |
| 6 | 2-2 | Blue | −11 | 25 | This invention |

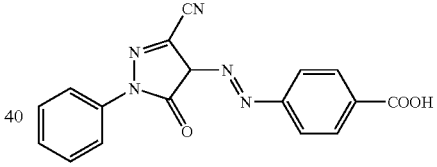

Dye for comparison 1

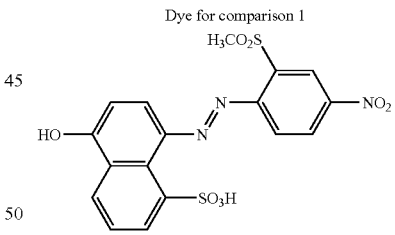

Dye for comparison 2

Test Example

Test for Resistance to Washing and Light

Each bundle of hairs, after the dyeing process was finished, was washed and then dried, to observe the color of the bundle of hairs. Then, the ΔΔE*$_{ab}$ value, which was the variation in the ΔE*$_{ab}$ of each bundle of hairs after it was colored in the above Example 1 and washed with a shampoo 20 times, was measured, and the results of the ΔΔE*$_{ab}$ value are shown in Table 2. A hair-dyeing agent 7 (for comparison) was prepared, which had the same composition as that of Example 1, except that the following Dye for comparison 3 was used as the dye, and a bundle of hairs was subjected to the dyeing and test in the same manner as in Example 1 using this hair-dyeing agent 7. The results are shown together.

TABLE 2

| Hair-dyeing agent | Dye | $\Delta\Delta E^*_{ab}$ | Remarks |
|---|---|---|---|
| 7 | Dye for comparison 3 | 20 | Comparative example |
| 3 | 1-1 | 3 | This invention |
| 4 | 1-8 | 4 | This invention |
| 5 | 1-10 | 6 | This invention |
| 6 | 2-2 | 4 | This invention |

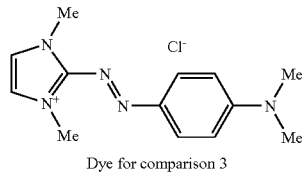

Dye for comparison 3

Table 2 shows that the hair-dyeing agent of the present invention showed remarkably higher resistance to washing compared with Hair-dyeing agent 7 for comparison.

Further, the hair-dyeing agents of the present invention, which were prepared using the compounds represented by formula (1) or (2), all showed the same light fastness as, or higher light fastness than, the hair-dyeing agents prepared from Dyes for comparison 1 and 2, in the color-fading test using sunlight.

Having described my invention as related to the present embodiments, it is my intention that the invention not be limited by any of the details of the description, unless otherwise specified, but rather be construed broadly within its spirit and scope as set out in the accompanying claims.

What I claim is:

1. A hair-dyeing agent, comprising at least one compound represented by formula (1) as a dye:

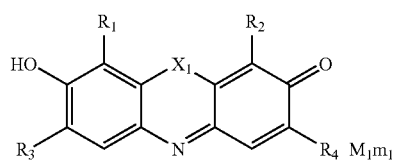

Formula (1)

wherein $X_1$ represents an oxygen atom, a nitrogen atom, a sulfur atom, or a dialkylmethylene group; $R_1$, $R_2$, $R_3$, and $R_4$ each independently represent a hydrogen atom or a substituent; $M_1$ represents a counter ion to balance the charge of the molecule; and $m_1$ denotes a number of 0 or more necessary to neutralize said charge of the molecule, and flirther comprising an oxidizing agent.

2. The hair-dyeing agent according to claim 1, wherein $R_1$, $R_2$, $R_3$, and $R_4$ each independently represent a hydrogen atom, or a group or atom selected from the group consisting of a halogen atom, an alkyl group, a cycloalkyl group, a bicycloalkyl group, a tricycloalkyl group, an alkenyl group, a cycloalkenyl group, a bicycloalkenyl group, an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group, an ammonio group, an acylamino group, an aminocarbonylamino group, an alkoxycarbonylamino group, an aryloxycarbonylamino group, a sulfamoylamino group, an alkyl- or aryl-sulfonylamino group, a mercapto group, an alkythio group, an arylthio group, a heterocyclic thio group, a sulfamoyl group, a sulfo group, an alkyl- or aryl-sulfinyl group, an alkyl- or aryl-sulfonyl group, an acyl group, an alkoxycarbonyl group, an aryloxycarbonyl group, a carbamoyl group, an aryl- or heterocyclic-azo group, an imido group, a phosphino group, a phosphinyl group, a phosphinyloxy group, a phosphinylamino group, a phosphono group, a silyl group, a hydrazino group, and a ureido group.

3. The hair-dyeing agent according to claim 1, wherein $R_1$, $R_2$, $R_3$, and $R_4$ each independently represent a hydrogen atom, or a group or atom selected from the group consisting of a halogen atom, alkyl group, hydroxyl group, amino group, alkoxy group, alkylthio group, aryloxy group, arylthio group, acyl group, cyano group, or nitro group.

4. The hair-dyeing agent according to claim 1, wherein $R_1$, $R_2$, $R_3$ and $R_4$ each independently represent a hydrogen atom or a halogen atom.

5. The hair-dyeing agent according to claim 1, wherein $R_1$, $R_2$, $R_3$ and $R_4$ each independently represent a hydrogen atom or a halogen atom; and $X_1$ represents an oxygen atom or a dialkylmethylene group.

6. The hair-dyeing agent according to claim 1, wherein the dye is a direct dye.

7. A hair-dyeing agent, comprising at least one compound represented by formula (2) as a dye:

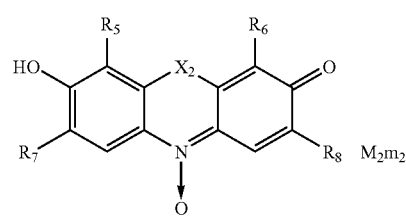

Formula (2)

wherein $X_2$ represents an oxygen atom, a nitrogen atom, a sulfur atom, or a dialkylmethylene group; $R_5$, $R_6$, $R_7$, and $R_8$ each independently represent a hydrogen atom or a substituent; $M_2$ represents a counter ion to balance the charge of the molecule; and $m_2$ denotes a number of 0 or more necessary to neutralize said charge of the molecule, and further comprising an oxidizing agent.

8. The hair-dyeing agent according to claim 7, wherein $R_5$, $R_6$, $R_7$, and $R_8$ each independently represent a hydrogen atom, or a group or atom selected from the group consisting of a halogen atom, an alkyl group, a cycloalkyl group, a bicycloalkyl group, a tricycloalkyl group, an alkenyl group, a cycloalkenyl group, a bicycloalkenyl group, an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group, an ammonio group, acylamino group, an aminocarbonylamino group, an alkoxycarbonylamino group, an aryloxycarbonylamino group, a sulfamoylamino group, an alkyl- or aryl-sulfonylamino group, a mercapto group, an alkylthio group, an arylthio group, a heterocyclic thio group, a sulfamoyl group, a sulfo group, an alkyl- or aryl-sulfinyl group, an alkyl- or aryl-sulfonyl group, an acyl group, an alkoxycarbonyl group, an aryloxycarbonyl group, a carbamoyl group, an aryl- or heterocyclic-azo group, an imido group, a phosphino group, a phosphinyl group, a phosphinyloxy group, a phosphinylamino group, a phosphono group, a silyl group, a hydrazino group, and a ureido group.

9. The hair-dyeing agent according to claim 7, wherein $R_5$, $R_6$, $R_7$, and $R_8$ each independently represent a hydrogen atom, or a group or atom selected from the group consisting of a halogen atom, alkyl group, hydroxyl group, amino group, alkoxy group, alkylthio group, aryloxy group, arylthio group, acyl group, cyano group, or nitro group.

10. The hair-dyeing agent according to claim 7, wherein $R_5$, $R_6$, $R_7$, and $R_8$ each independently represent a hydrogen atom or a halogen atom.

11. The hair-dyeing agent according to claim 7, wherein $R_5$, $R_6$, $R_7$, and $R_8$ each independently represent a hydrogen atom or a halogen atom; and $X_2$ represents an oxygen atom or a dialkylmethylene group.

12. The hair-dyeing agent according to claim 7, wherein the dye is a direct dye.

13. A method of dyeing hair, which comprises applying a hair-dyeing agent comprising at least one compound represented by formula (1) as a dye:

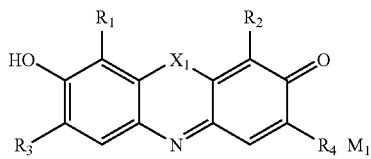

Formula (1)

wherein $X_1$ represents an oxygen atom, a nitrogen atom, a sulfur atom, or a dialkylmethylene group; $R_1$, $R_2$, $R_3$ and $R_4$ each independently represent a hydrogen atom or a substituent; $M_1$ represents a counter ion to balance the charge of the molecule; and $m_1$ denotes a number of 0 or more necessary to neutralize said charge of the molecule, wherein the hair-dyeing agent further comprises an oxidizing agent.

14. The method of dyeing hair according to claim 13, wherein $R_1$, $R_2$, $R_3$, and $R_4$ each independently represent a hydrogen atom, or a group or atom selected from the group consisting of a halogen atom, an alkyl group, a cycloalkyl group, a bicycloalkyl group, a tricycloalkyl group, an alkenyl group, a cycloalkenyl group, a bicycloalkenyl group, an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group, an ammonio group, an acylamino group, an aminocarbonylamino group, an alkoxycarbonylamino group, an aryloxycarbonylamino group, a sulfamoylamino group, an alkyl- or aryl-sulfonylamino group, a mercapto group, an alkylthio group, an arylthio group, a heterocyclic thio group, a sulfamoyl group, a sulfo group, an alkyl- or aryl-sulfinyl group, an alkyl- or aryl-sulfonyl group, an acyl group, an alkoxycarbonyl group, an aryloxycarbonyl group, a carbamoyl group, an aryl- or heterocyclic-azo group, an imido group, a phosphino group, a phosphinyl group, a phosphinyloxy group, a phosphinylamino group, a phosphono group, a silyl group, a hydrazino group, and a ureido group.

15. The method of dyeing hair according to claim 13, wherein $R_1$, $R_2$, $R_3$, and $R_4$ each independently represent a hydrogen atom, or a group or atom selected from the group consisting of a halogen atom, alkyl group, hydroxyl group, amino group, alkoxy group, alkylthio group, aryloxy group, arylthio group, acyl group, cyano group, or nitro group.

16. The method of dyeing hair according to claim 13, wherein $R_1$, $R_2$, $R_3$ and $R_4$ each independently represent a hydrogen atom or a halogen atom.

17. The method of dyeing hair according to claim 13, wherein $R_1$, $R_2$, $R_3$ and $R_4$ each independently represent a hydrogen atom or a halogen atom; and $X_1$ represents an oxygen atom or a dialkylmethylene group.

18. The method of dyeing hair according to claim 13, wherein the dye is a direct dye.

19. A method of dyeing hair, which comprises applying a hair-dyeing agent comprising at least one compound represented by formula (2) as a dye:

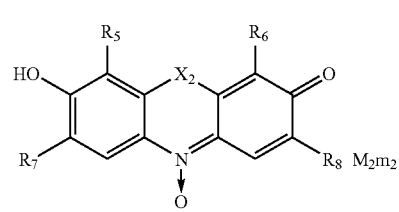

Formula (2)

wherein $X_2$ represents an oxygen atom, a nitrogen atom, a sulfur atom, or a dialkylmethylene group; $R_5$, $R_6$, $R_7$, and $R_8$ each independently represent a hydrogen atom or a substituent; $M_2$ represents a counter ion to balance the charge of the molecule; and $m_2$ denotes a number of 0 or more necessary to neutralize said charge of the molecule, wherein the hair-dyeing agent further comprises an oxidizing agent.

20. The method of dyeing hair according to claim 19, wherein $R_5$, $R_6$, $R_7$, and $R_8$ each independently represent a hydrogen atom, or a group or atom selected from the group consisting of a halogen atom, an alkyl group, a cycloalkyl group, a bicycloalkyl group, a tricycloalkyl group, an alkenyl group, a cycloalkenyl group, a bicycloalkenyl group, an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group, an ammonio group, an acylamino group, an aminocarbonylamino group, an alkoxycarbonylamino group, an aryloxycarbonylamino group, a sulfamoylamino group, an alkyl- or aryl-sulfonylamino group, a mercapto group, an alkylthio group, an arylthio group, a heterocyclic thio group, a sulfamoyl group, a sulfo group, an alkyl- or aryl-sulfinyl group, an alkyl- or aryl-sulfonyl group, an acyl group, an alkoxycarbonyl group, an aryloxycarbonyl group, a carbamoyl group, an aryl- or heterocyclic-azo group, an imido group, a phosphino group, a phosphinyl group, a phosphinyloxy group, a phosphinylamino group, a phosphono group, a silyl group, a hydrazino group, and a ureido group.

21. The method of dyeing hair according to claim 19, wherein $R_5$, $R_6$, $R_7$, and $R_8$ each independently represent a hydrogen atom, or group or atom selected from the group consisting of a halogen atom, alkyl group, hydroxyl group, amino group, alkoxy group, alkylthio group, aryloxy group, arylthio group, acyl group, cyano group, or nitro group.

22. The method of dyeing hair according to claim 19, wherein $R_5$, $R_6$, $R_7$, and $R_8$ each independently represent a hydrogen atom or a halogen atom.

23. The method of dyeing hair according to claim 19, wherein $R_5$, $R_6$, $R_7$, and $R_8$ each independently represent a hydrogen atom or a halogen atom; and $X_2$ represents an oxygen atom or a dialkylmethylene group.

24. The method of dyeing hair according to claim 19, wherein the dye is a direct dye.

* * * * *